(12) United States Patent
Siccardi et al.

(10) Patent No.: US 12,208,022 B2
(45) Date of Patent: Jan. 28, 2025

(54) POSITIONING DEVICE OF A SURGICAL INSTRUMENT FOR HIP ARTHROPLASTY SURGERY

(71) Applicant: MEDACTA INTERNATIONAL SA, Castel San Pietro (CH)

(72) Inventors: Francesco Siccardi, Castel San Pietro (CH); Massimiliano Bernardoni, Castel San Pietro (CH); Christian Trombetta, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 493 days.

(21) Appl. No.: 17/432,172

(22) PCT Filed: Feb. 20, 2020

(86) PCT No.: PCT/IB2020/051419
§ 371 (c)(1),
(2) Date: Aug. 19, 2021

(87) PCT Pub. No.: WO2020/170184
PCT Pub. Date: Aug. 27, 2020

(65) Prior Publication Data
US 2022/0183857 A1 Jun. 16, 2022

(30) Foreign Application Priority Data
Feb. 21, 2019 (IT) .................. 102019000002543

(51) Int. Cl.
*A61F 2/46* (2006.01)

(52) U.S. Cl.
CPC .................. *A61F 2/4609* (2013.01)

(58) Field of Classification Search
CPC ........ A61F 2/4609; A61F 2/46; A61F 2/4603; A61F 2/4607; A61F 2/4637;
(Continued)

(56) References Cited

U.S. PATENT DOCUMENTS 5,346,496 A 9/1994 Pennig
6,231,611 B1 * 5/2001 Mosseri ............... A61F 2/4607
623/23.11
(Continued)

FOREIGN PATENT DOCUMENTS

EP 3298972 A2 3/2018
WO 98/34555 A1 8/1998

OTHER PUBLICATIONS

International Search Report and Written Opinion, issued by the International Searching Authority (ISA/EP) in PCT Application No. PCT/IB2020/051419 on Jun. 3, 2020. 8 pages.

*Primary Examiner* — Tracy L Kamikawa
(74) *Attorney, Agent, or Firm* — Meunier Carlin & Curfman LLC

(57) ABSTRACT

Various implementations include a positioning device of a surgical instrument for hip arthroplasty surgery that includes an arched structure having a first and a second end, wherein the first end can be positioned inside a patient, a gripping element located at the second end of the arched structure, a surgical instrument that can be coupled to the gripping element at a seat made in this gripping element, and a positioning and fixing head arranged at the first end of the arched structure.

17 Claims, 21 Drawing Sheets

(58) Field of Classification Search
CPC ...... A61F 2002/4625; A61F 2002/4627; A61F 2002/4628; A61F 2002/4635; A61B 17/1742; A61B 17/1746; A61B 17/175; A61B 17/1725
See application file for complete search history.

(56) References Cited

U.S. PATENT DOCUMENTS

| | | |
|---|---|---|
| 6,905,502 B2 | 6/2005 | Penenberg |
| 7,588,578 B2 * | 9/2009 | Triplett .............. A61B 17/1671 33/512 |
| 7,833,229 B2 | 11/2010 | Penenberg |
| 8,925,235 B2 * | 1/2015 | Buie, II .................. F41A 29/02 42/95 |
| 9,241,744 B2 * | 1/2016 | Blake ................. A61B 17/7225 |
| 9,289,313 B2 * | 3/2016 | Preuss ................ A61B 17/8872 |
| 9,668,791 B2 * | 6/2017 | Khong .............. A61B 17/7283 |
| 9,763,678 B2 * | 9/2017 | O'Neil .................. A61M 29/02 |
| 2007/0270973 A1 * | 11/2007 | Johnson ................ A61F 2/4609 623/17.16 |
| 2012/0277745 A1 * | 11/2012 | Lizee ................. A61B 17/1739 606/59 |
| 2015/0313722 A1 * | 11/2015 | Hudak, Jr. ............ A61F 2/4609 606/99 |
| 2017/0086966 A1 * | 3/2017 | Spenciner ............. A61F 2/0811 |
| 2018/0242988 A1 * | 8/2018 | Dacosta ............. A61B 17/1717 |

* cited by examiner

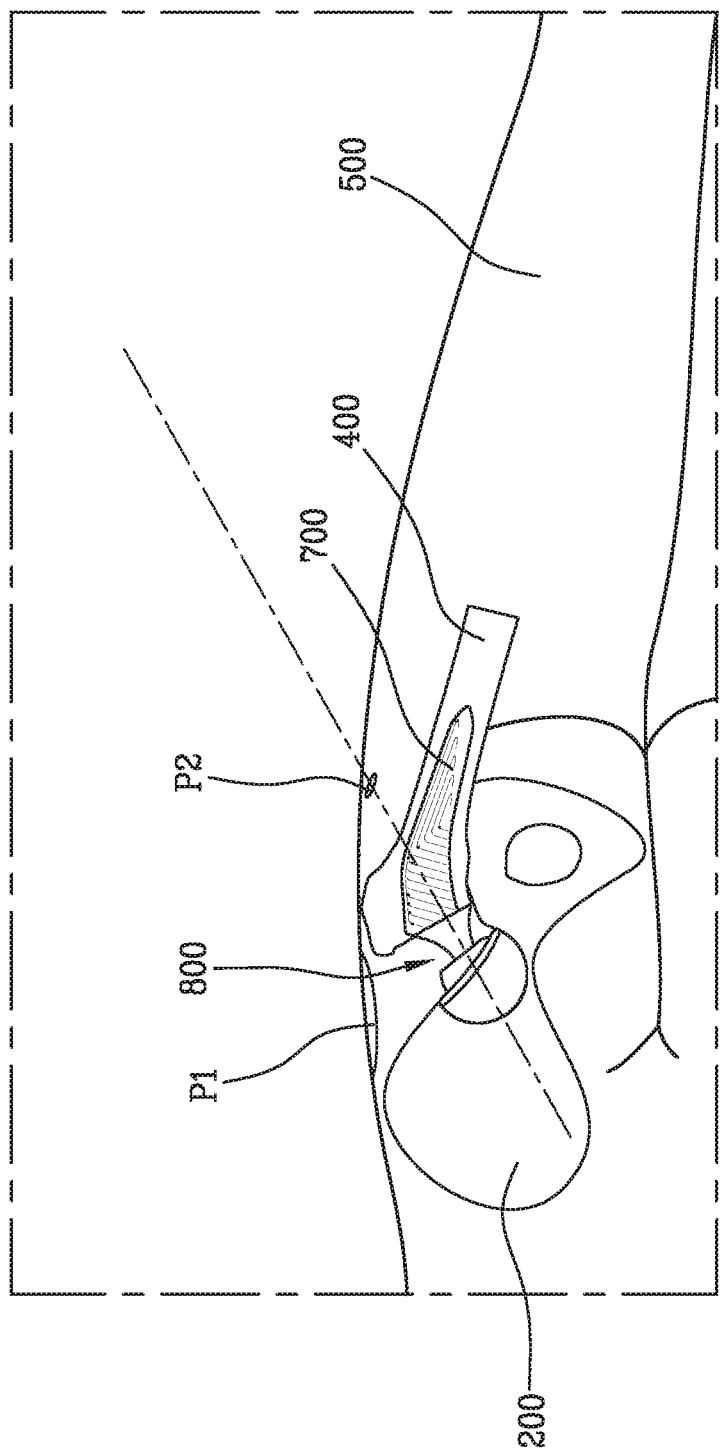

POSITIONING DEVICE OF A SURGICAL INSTRUMENT FOR HIP ARTHROPLASTY SURGERY

TECHNICAL FIELD

This invention concerns a positioning device of a surgical instrument for hip arthroplasty surgery.

Good long-term results in total hip arthroplasty (THA) can be achieved using a variety of surgical techniques. Traditionally, front, side, or rear approaches are used. With the exception of the front approach, all the others have the unfortunate drawback of affecting the iliotibial band, leading to longer recovery times for patients.

The iliotibial (ITB) band (or tract) is the tendon that connects to two muscles: the large gluteus and the tensor fasciae latae muscle. It is a group of vertically oriented fibres that converge at the iliac crest, at the iliac tubercle, and inserts at the fibula.

In other words, it inserts onto the outer face of the tibia, just below the knee joint. In its course, it passes over a bone protuberance called the lateral epicondyle, from which it is separated by a sliding synovial bursa.

It is a reinforcement band that stabilises the flexor and extensor muscles of the leg. Affecting this structure has repercussions on the hip as well as on the knee joint, and it can lead to more demanding, painful surgeries and longer recovery times for the patient.

Therefore, the drive to contain costs and to meet higher patient expectations has shifted the focus to improving short-term outcomes, such as length of stay in hospital and the use of lower doses of hospital painkillers or narcotics.

PRIOR ART

In recent years, a superolateral surgery has been developed that avoids any interaction with the iliotibial band, allowing a rapid, safe, and minimally invasive surgery and a significantly reduced recovery time for the patient.

A superolateral technique currently used is described, for example, in U.S. Pat. No. 6,905,502 and in U.S. Pat. No. 7,833,229. This technique involves the use of a support arm and of a marker that defines the entry point of a surgical instrument. This arm connects to the acetabular cup and is shaped so as to orient the marker in the correct insertion direction for the instrument.

However, the applicant has found that such an approach causes some drawbacks.

In particular, the connection of the arm with the acetabular cup makes the connection of the entire device unstable because the reference point is an element that is detached from the element on which you want to operate.

In other words, the connection takes place at the acetabular cup but the insertion point of the instrument is on the leg and, therefore, at the level of the femur. This creates a degree of instability in inserting the instrument.

In addition, since, for hip arthroplasty surgery, the surgeon has to operate on the acetabular cup, the latter is obstructed by the direct connection with the reference arm that keeps the instrument in position.

Furthermore, this technique involves the use of a cannula inside of which the various surgical instruments are inserted in sequence. The presence of the cannula can create additional problems in obstructing the field of vision, in addition to lengthening the operating times for replacing the surgical instrument.

There are known devices for guiding the insertion of screws into the femoral neck, as described in U.S. Pat. No. 5,346,496, or to insert intramedullary nails into the femoral bone, as described in EP 3298972.

The purpose of this invention is to overcome the drawbacks of the prior art.

In particular, the purpose of this invention is to propose a positioning device of a surgical instrument for hip arthroplasty surgery that ensures good stability of the instrument and does not obstruct the surgeon's field of vision.

Another purpose of this invention is to provide a positioning device of a surgical instrument for hip arthroplasty surgery that is easy for the surgeon to use and allows quick and safe operations for the patient.

Finally, the purpose of this invention is to provide an instrument that can be configured as a correct and precise reference in relation to the patient's anatomy during hip replacement operations.

These and other purposes and advantages are achieved with a positioning device of a surgical instrument for hip arthroplasty surgery according to what is described in the appended claims.

SUMMARY

A first aspect of this invention involves a positioning device of a surgical instrument for hip arthroplasty surgery comprising an arched structure with a first and second end. The arched structure is preferably open so that the first end can be positioned inside a patient and the second end remains outside the patient; this second end is, advantageously, equipped with a gripping element.

The surgical instrument can be coupled to the gripping element at a seat, at least partially open or closed in the slot, made in the gripping element itself.

A positioning and fixing head is arranged at the first end of the arched structure and has connection means to connect to a stem that can be inserted into a femoral canal.

The positioning and fixing head lies on a plane that is tilted in relation to the first end of the arched structure, in particular in relation to a longitudinal axis of a first section of the arched structure. This tilting angle of the positioning and fixing head in relation to the first end ranges between 5° and 85°, preferably 45°.

These connection means of the positioning and fixing head face and are oriented towards the gripping element, precisely to couple with the stem that can be inserted inside the patient's femoral canal, particularly at the femoral neck.

The connection means comprise a snap connection or snap fit. The positioning and fixing head has a zero position in normal use in which it faces the gripping element and the connection means are axially cut by a plane that passes through a longitudinal symmetry axis of the arched structure.

At the zero position, the connection means of the positioning and fixing head are aligned with the gripping element seat, inside of which a stem, which is slidably movable, can be inserted. The positioning and fixing head has a degree of rotational freedom about the longitudinal symmetry axis of the arched structure that allows the positioning and fixing head to travel 8 at + or −20° in relation to the zero position thereof.

The arched structure is shaped and sized in such a way as to position the second end above the patient's femur, on the outer side of the leg.

The surgical instrument comprises a plurality of interchangeable heads that can be joined to the stem.

The surgical instrument has a slidably movable stem inside the seat.

The stem is joined to the gripping element so that it can be oriented basically towards the positioning and fixing head, in particular towards the connection means when the head is in the zero position, defining an insertion angle ranging between 30° and 60°, preferably 45°, in relation to a longitudinal symmetry axis of the gripping element. The insertion angle α is also at 45° in relation to the patient's pelvic plane.

The stem may have a degree of rotational freedom about an axis that is orthogonal both to the stem itself and to a longitudinal axis of the gripping element; this degree of rotational freedom enables the stem to travel an angle β ranging between −15° and +105° in relation to the insertion angle α.

The gripping element has a circular graduated scale indicating the rotational travel angles of the stem.

The gripping element has at least a first degree of translational freedom in relation to arched structure along a longitudinal axis thereof. Preferably, the longitudinal axis of the gripping element coincides, along the length of the gripping element itself, with the longitudinal axis of the arched structure.

The gripping element has at least a second degree of rotational freedom about a longitudinal symmetry axis thereof. The degree of rotational freedom enables the gripping element to travel about a longitudinal symmetry axis at an angle δ of + or −15° in relation to a position of normal use at which the stem belongs to a plane containing the arched structure.

The arched structure is open and has at least a first, a second, and third straight segment.

The first and said second straight segments are orthogonally connected in sequence to each other with a respective arched portion, just as the second and third straight segments are orthogonally connected in sequence to each other with a respective arched portion.

In a second aspect, the invention concerns a surgical method for hip arthroplasty.

The method involves the steps of placing the patient so that they are lying on their side. Locating the incision point above the acetabular cup and making a first cut on the patient's skin. Freeing the femoral area from the piriformis muscle and joint tendon. Proceeding with the cortical opening of the upper femur and then reaming the femur in the proximal area. Rasping the femoral canal in both distal and proximal positions. Then the femoral neck is cut and the femoral head is removed from the acetabulum. Preferably, the distal femur is trimmed.

From the first incision point, locating the second incision point through which to insert a surgical instrument borne by the arched structure. Making a second incision at the identified spot.

At this point, a temporary stem is inserted into the femoral canal to which the connection means of the positioning and fixing head, which is positioned at the first end of the positioning device's arched structure, are connected. The temporary stem is inserted through the femoral neck, severed from the rest of the femur.

The positioning device of a surgical instrument for hip arthroplasty surgery comes out of the patient bringing the second end of the arched structure into the correct position outside the patient's leg, above the femur, on the outer side of the leg, i.e. on the side not facing the other leg. Aligning the surgical instrument, the stem of which is tilted at 45° in relation to the pelvic plane, and inserting the instrument stem through the second incision.

Advancing the stem inside the patient up to the acetabular cup and inserting, through the first incision, a first surgical tool to be connected to the stem. The first surgical tool is preferably a rasp for smoothing the acetabular cup. Subsequently, the first surgical tool is replaced with a second surgical tool that may be designed to impact an acetabular cup prosthesis inside the acetabulum, after having arranged the acetabular cup prosthesis in place.

Removing the surgical tool, the stem, the positioning device, and the temporary stem from the femoral canal to insert a definitive stem into the canal and attaching it to the newly positioned prosthesis inside the acetabulum to position the final implant.

BRIEF DESCRIPTION OF THE FIGURES

A positioning device of a surgical instrument for hip arthroplasty surgery as described and claimed is also shown in the following figures that are intended to be illustrative and not exhaustive, wherein:

FIGS. 7-21 show different steps in the operating method during which the device of this invention is used.

DETAILED DESCRIPTION

Figure 1:
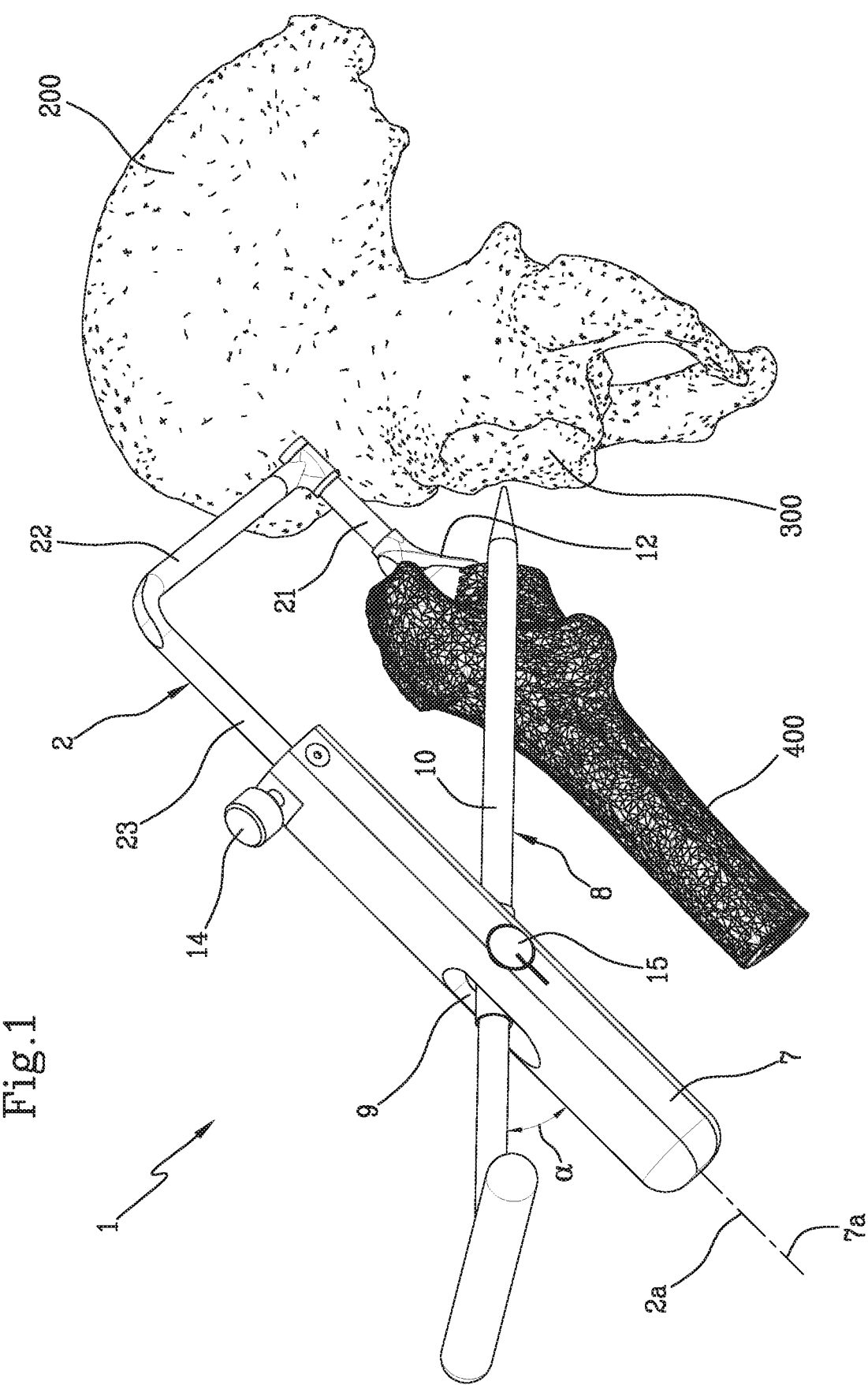
FIG. 1 is a perspective view of a positioning device of a surgical instrument for hip arthroplasty surgery, according to this invention, operating on a femoral bone and a hip.

With reference to the attached figures, the reference number 1 indicates a positioning device of a surgical instrument for hip arthroplasty surgery 200. In detail, this device is used for correctly positioning and orienting a surgical instrument for hip arthroplasty 200, i.e. to correctly direct the different surgical instruments 11 needed during the hip joint replacement operation to the acetabular cup 300.

Figure 4:
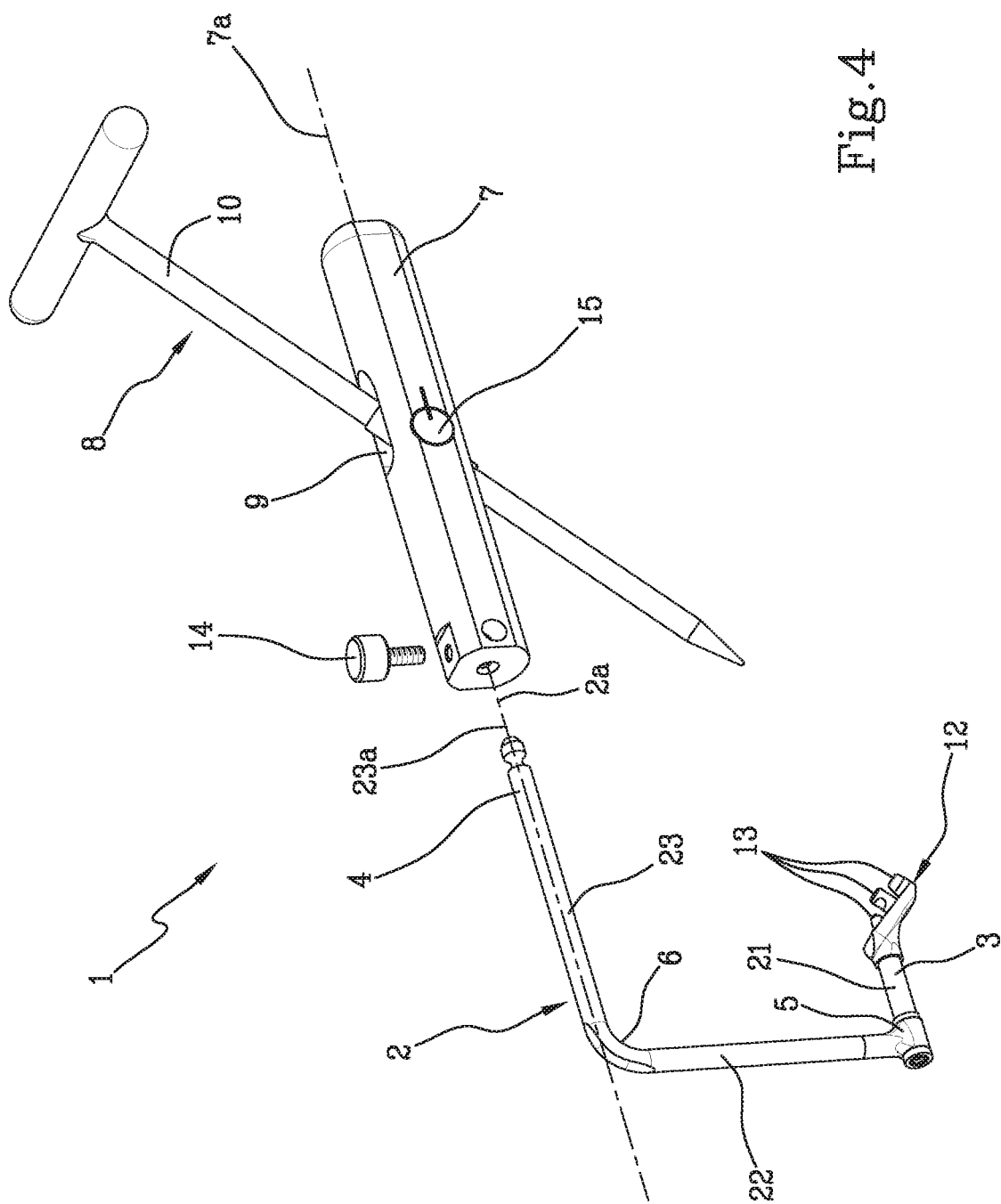
FIG. 4 is a partially exploded view of the device that is the subject of this invention to better illustrate the components thereof.
Figure 5:
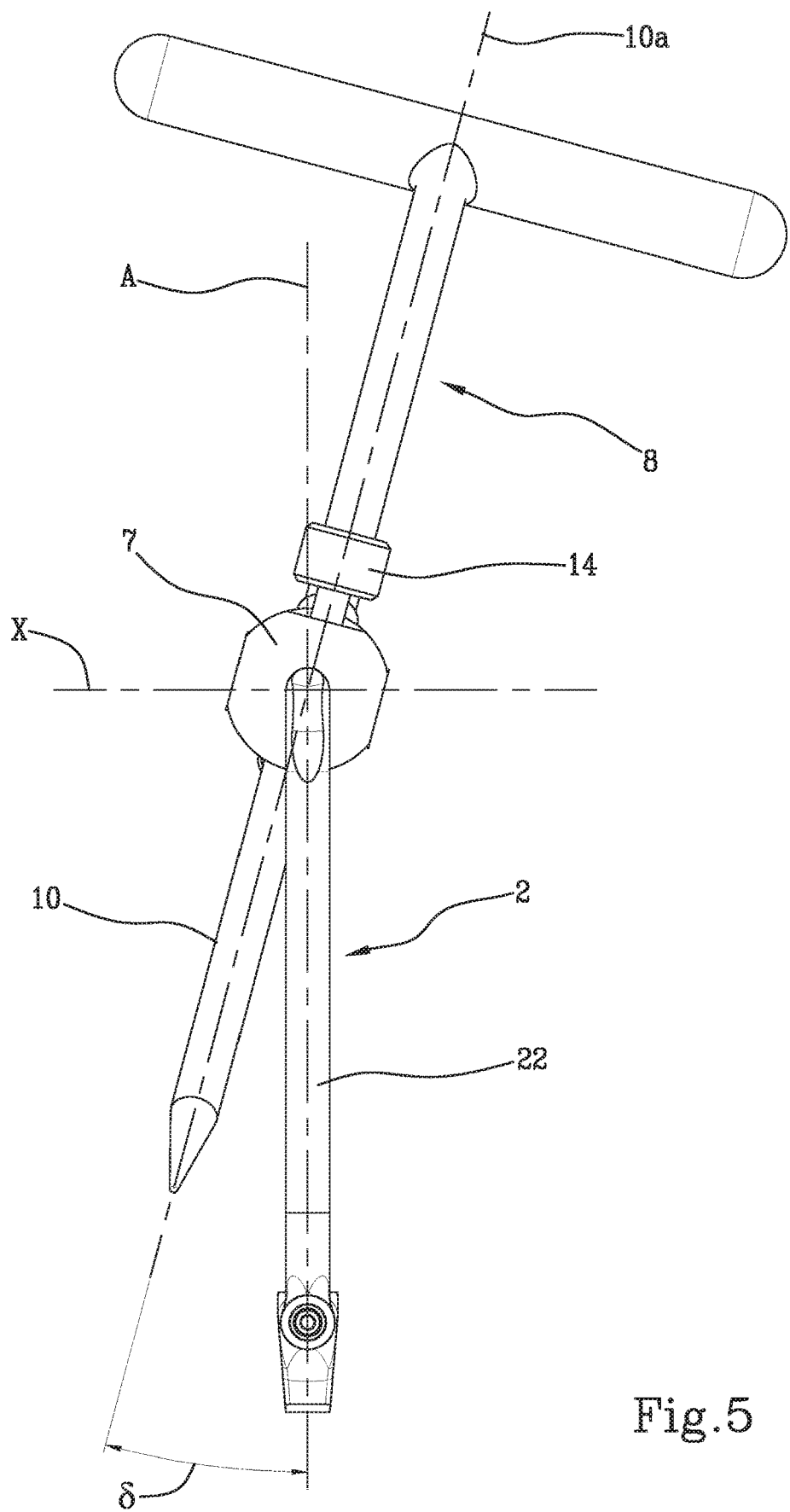
FIGS. 5 and 6 are front views of the device that is the subject of this invention in other operating positions.

This device comprises an arched structure 2 that has a first 3 and a second 4 end (visible in FIG. 4).

In particular, the first end 3 can be positioned inside a patient 500, while the second end 4 remains outside the patient 500. In particular, the second end remains outside the patient, on the outer side of the leg, i.e. the side not facing the pelvic area.

Advantageously, this arched structure 2 is open and has, preferably, at least a first 21, a second 22, and a third 23 straight segment placed between them in sequence. Even more preferably, the first 21 and the second 22 straight segment are orthogonally connected in sequence with each other using a respective arched portion 5, just as the second 22 and the third 23 straight segment are orthogonally connected in sequence with each other by means of a respective arched portion 6.

The first section 21 preferably starts at the first end 3, while the third section 23 ends with the second end 4 of the arched structure 2.

In addition, the device 1 comprises a gripping element 7, or handle, located at the second end 4 of the arched structure 2, for which the surgeon can grasp and handle the device itself 1.

At the first end 3, the device 1 comprises a positioning and fixing head 12; this head 12 has connection means 13 facing the gripping element 7 to couple with a temporary stem 100 that can be inserted inside a femoral canal 600 of a femur 400 of a patient 500. The temporary stem 100 can be inserted into the femoral canal through the femoral neck that is cut, separating it from the rest of the femoral bone.

In other words, the positioning and fixing head 12 faces the opposite direction to the acetabular cup 300.

Advantageously, these connection means 13 comprise a snap connection or snap fit, or a joint, interference, or push-button connection, or the like, to quickly join inside their respective seats made in the temporary stem 100 that can be inserted into the femoral canal 600.

Once the first entry point P1 has been identified for the first end 3, this configuration, in particular the connection of the positioning and fixing head 12 to the temporary stem 100, allows the second end to be correctly positioned above the outer portion of the patient's leg.

In other words, the arched structure 2 is shaped and sized in such a way that the second end 4 is positioned above the patient's femur, outside the leg, i.e. facing the opposite direction to the pelvic area.

An alternative configuration (not depicted) to the arched structure composed of three straight segments as described above, could involve a semi-circular structure, where the first 3 and the second 4 ends are arranged at the extreme points of the diameter of the semicircle.

As can be seen in FIGS. 2-4 and 13-15, the positioning and fixing head 12 lies on a plane B that is tilted in relation to the first end 3 of the arched structure 2, in particular in relation to a longitudinal axis 3a of the first section 21 of the arched structure 2, of an angle φ. This tilting angle φ of the positioning and fixing head 12 in relation to the first end 3 ranges between 5° and 85°, preferably 45°. In this way, the connection means 13 are oriented and facing towards the gripping element 7.

The device 1 comprises, in addition, a surgical instrument 8 that can be coupled to the gripping element 7 at a seat 9 made in this gripping element 7. The seat 9 may be at least partially open or, alternatively, closed and shaped like a slot, as shown in the attached figures, purely by way of example.

A surgical instrument 8 can be coupled to the gripping element 7 at this seat 9.

In particular, the surgical instrument 8 comprises a stem 10 and a plurality of interchangeable tools or heads 11 that can be joined to the stem 10.

The interchangeable heads or tools 11 can be, for example, scalpels for making the incision in a given position, rasps to smooth the inside of the acetabular cup, or abutment heads to insert the prosthesis into the acetabular cup.

The stem 10 is slidably movable inside the above-mentioned seat 9 of the gripping element 7, so as to bring the joined tool closer or move it away from the acetabular cup 300, as will be explained in detail below. The stem 10 can be thus be brought closer or moved away from the positioning and fixing head 12.

Advantageously, the stem 10 is joined to the gripping element 7 so that it is basically oriented towards the positioning and fixing head 12, defining an insertion angle α ranging between 30° and 60°, preferably 45°, in relation to a longitudinal symmetry axis 7a of said gripping element 7.

In other words, the stem enters the patient at an angle of about 45° in relation to the pelvic plane of a patient.

The stem 10 of the surgical instrument 8 has a longitudinal symmetry axis 10a, transverse to the longitudinal symmetry axis 7a of the gripping element 7. The stem 10 is hinged to the gripping element 7 at the housing seat 9 and, therefore, has a degree of rotational freedom around an additional axis X that is orthogonal to both the axis 10a of the stem 10 and the longitudinal symmetry axis 7a of the gripping element 7.

Figure 2:
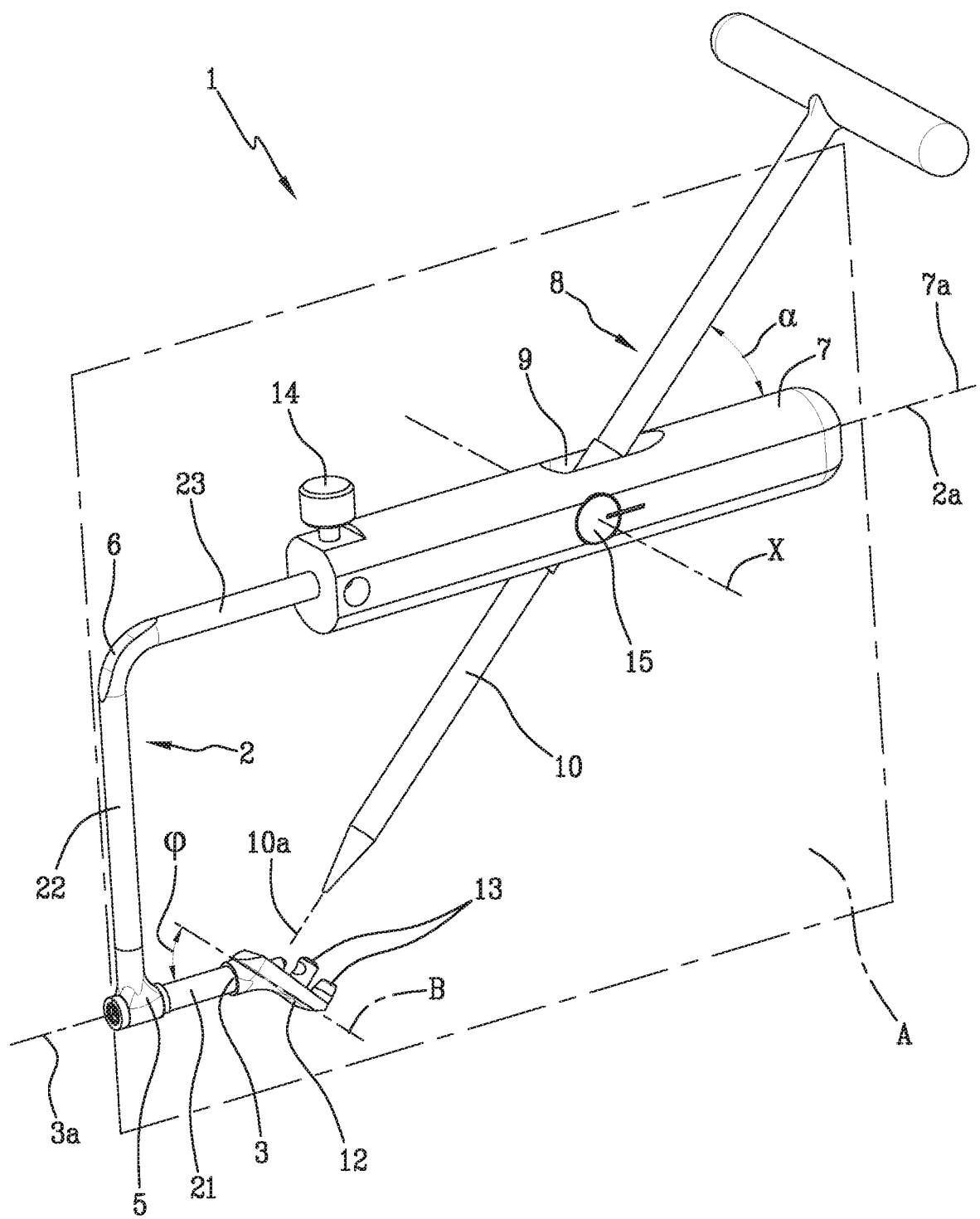
FIG. 2 is a perspective view of the device that is the subject of this invention, in a first operating configuration.
Figure 3:
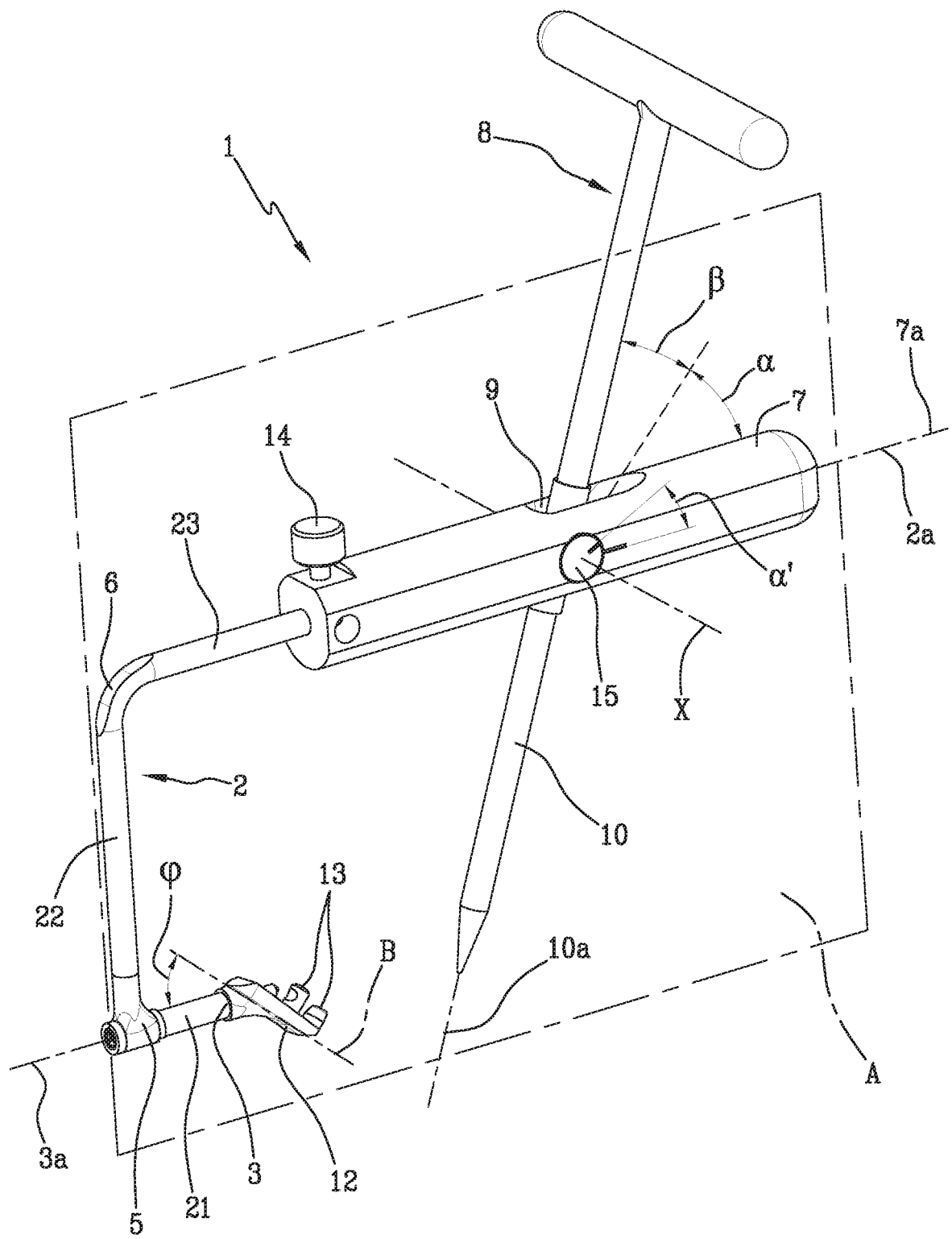
FIG. 3 is a perspective view of the device that is the subject of this invention, in a second operating configuration.

This degree of rotational freedom allows the stem 10 to travel around the axis X of an angle β (FIG. 3) ranging between −15° and +105° in relation to the insertion angle α. In order to check the tilt of the stem 10 in relation to the gripping element 7, a circular graduated scale 15 is provided on the gripping element 7, indicating the rotational travel angles of the stem 10. The zero of the circular graduated scale 15 (FIG. 2) is placed at 45° to the insertion angle α, as shown in FIG. 2. The angle α' (FIG. 3) on the graduated scale marks the angle of deviation of the stem 10 from the zero position of the stem 10 itself, which corresponds to an angle α=45° formed between the axis 10a of the stem 10 itself and the axis 7a of the gripping element 7.

The angle formed by the axis 10a of the stem 10 with the lying plane B of the positioning and fixing head 12 ranges between 30° and 150°, depending on the variable tilting of the stem 10 and on the angular position given to the positioning and fixing head 12 in relation to the end 3 of the arched structure 2.

The gripping element 7, positioned at the second end 4 of the arched structure 2, has at least a first degree of translational freedom in relation to the arched structure 2; in particular, it is slidably movable, at least partially, along the third straight segment 23 of the arched structure 2, along a longitudinal axis 7a of the gripping element itself coinciding with a longitudinal axis 23a of the arched structure 2. This freedom of translation is advantageously present to correctly align the stem 10, and, therefore, its axis 10a, with the acetabular cup 300 within which the tool that will be joined to the stem 10 must operate.

The need to adjust the distance of the gripping element 7 from the second straight segment 22 is basically due to the patient's size.

A fixing element 14, such as a pin or a screw, fixes the position of the gripping element 7 along the arched structure 2, in particular along the third straight segment 23 of this structure 2.

The gripping element 7 has, in addition, at least a second degree of rotational freedom about a longitudinal symmetry axis thereof 7a. This degree of rotational freedom enables the gripping element 7 to rotate about its longitudinal symmetry axis 7a at an angle δ of + or −15° in relation to a zero position of normal use at which the stem 10 belongs to a plane A containing the arched structure 2. In other words, the zero position of normal use of the gripping element 7 is configured when the stem is contained within the space of the arched structure 2.

The rotational freedom of the gripping element 7 also causes the stem 10 to oscillate by the same angular width. This is useful when proceeding with the engagement of the surgical instrument joined to the stem with fixing screws that are offset in relation to the central axis of the acetabular cup. It is therefore necessary that it be possible for it to travel with the stem 10, including to reach points not perfectly aligned with the central axis of the acetabular cup.

The positioning and fixing head 12 has a zero position in normal use (FIGS. 1-5) in which it faces the gripping element 7 and the connection means 13 are axially and centrally cut by one plane A containing the arched structure 2 and that passes through the symmetry axis 2a of the arched structure 2.

Figure 6:
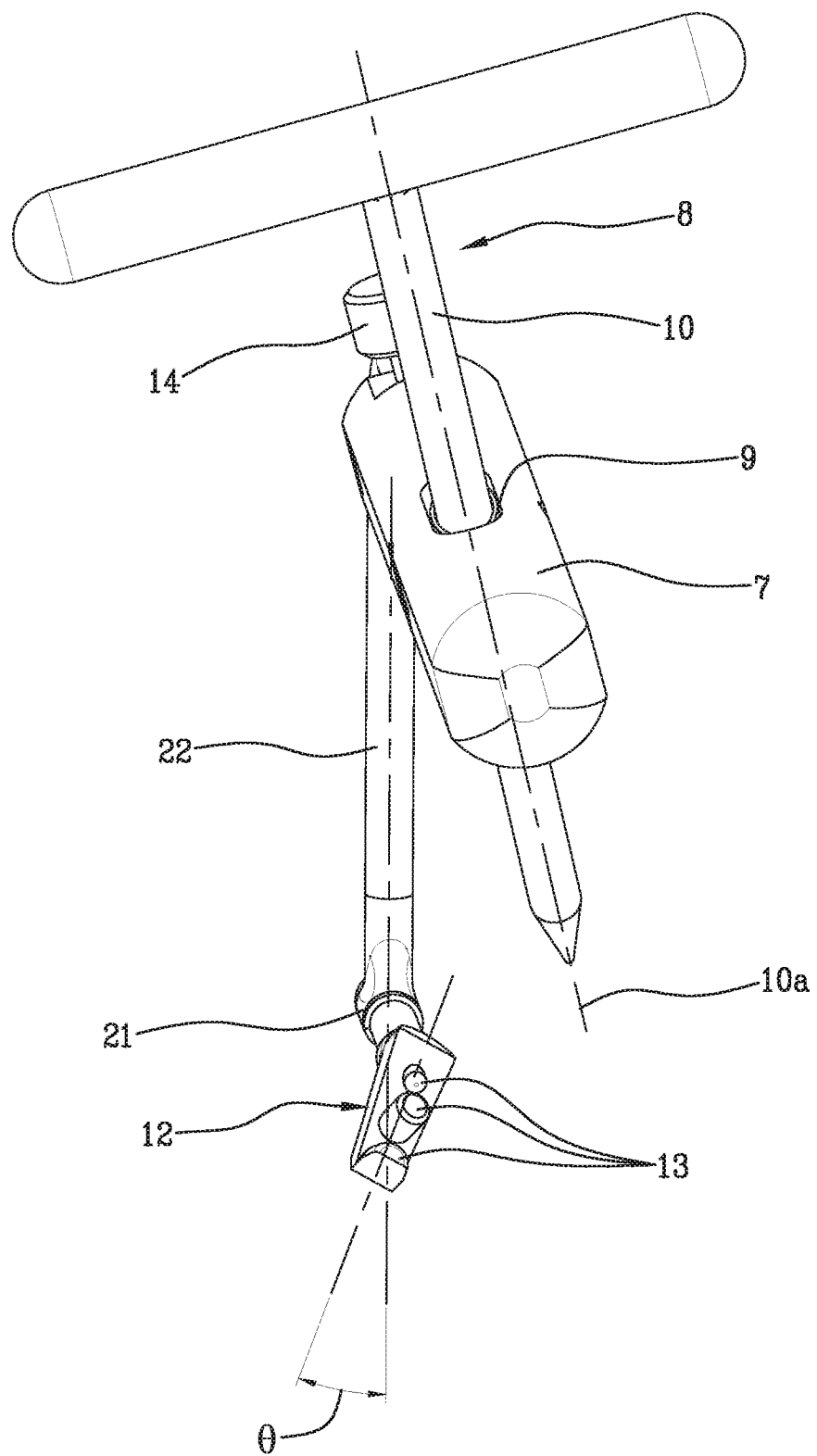
Figure 7:
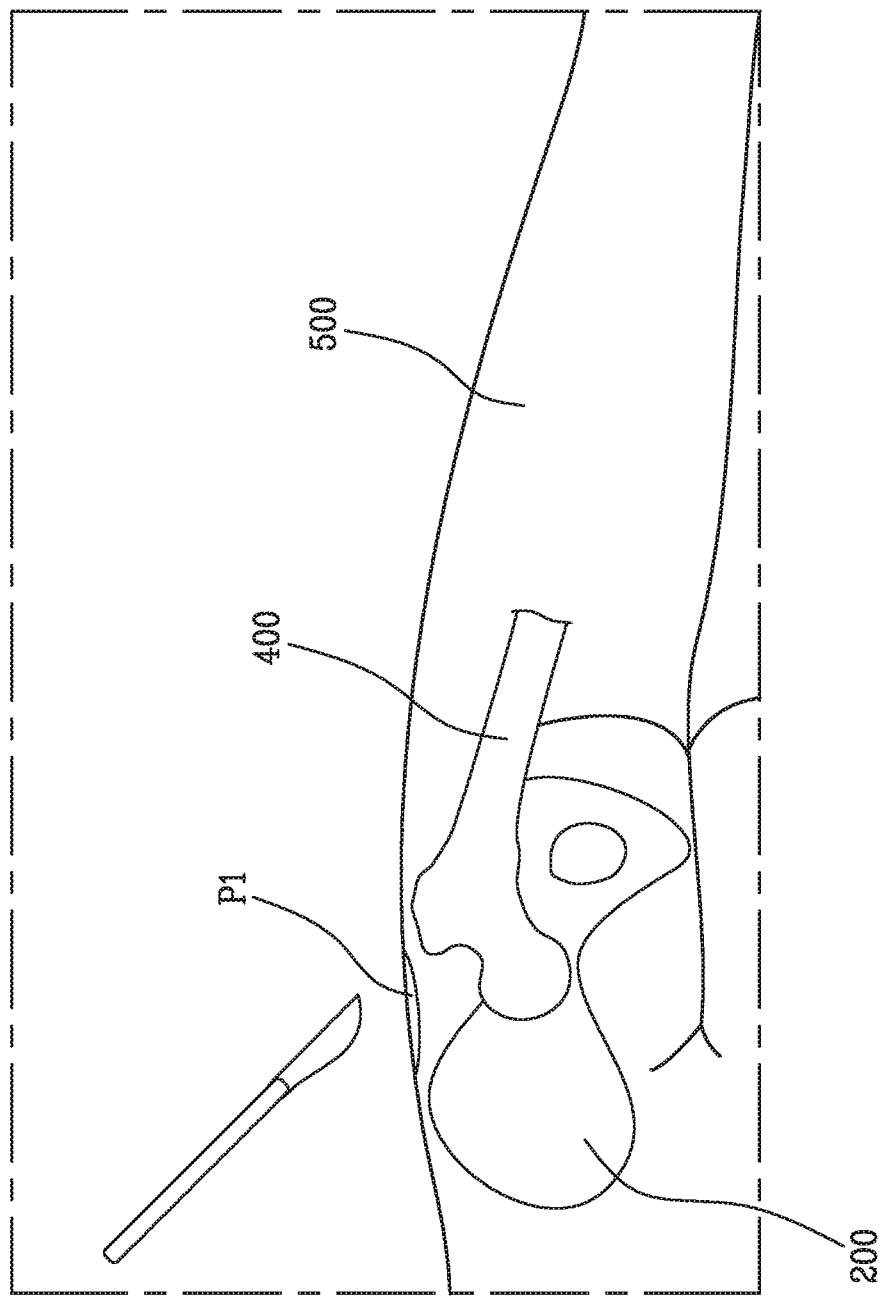

The positioning and fixing head 12 has a degree of rotational freedom about the longitudinal symmetry axis 2a of the arched structure 2 that allows it to travel according to an angle θ of about + or −20° in relation to the above-mentioned zero position (FIG. 6). This makes it possible to rotate the whole arched structure 2 in relation to the positioning and fixing head 12 that remains fixed and integral with the temporary stem 100 inserted inside the patient's femoral canal.

Optionally, there may be a sort of protective sheath (not shown) around the stem 10 that prevents any friction between the lateral surface of the stem 10 during its movement and the patient's surrounding tissues.

In use, the patient is placed in a lateral position, turning the side to be operated on to the surgeon who locates the point to make a first incision P1, positioned above the acetabular cup.

The piriformis tendon of the joint tendon is then cut to expose the femur.

Figure 8:
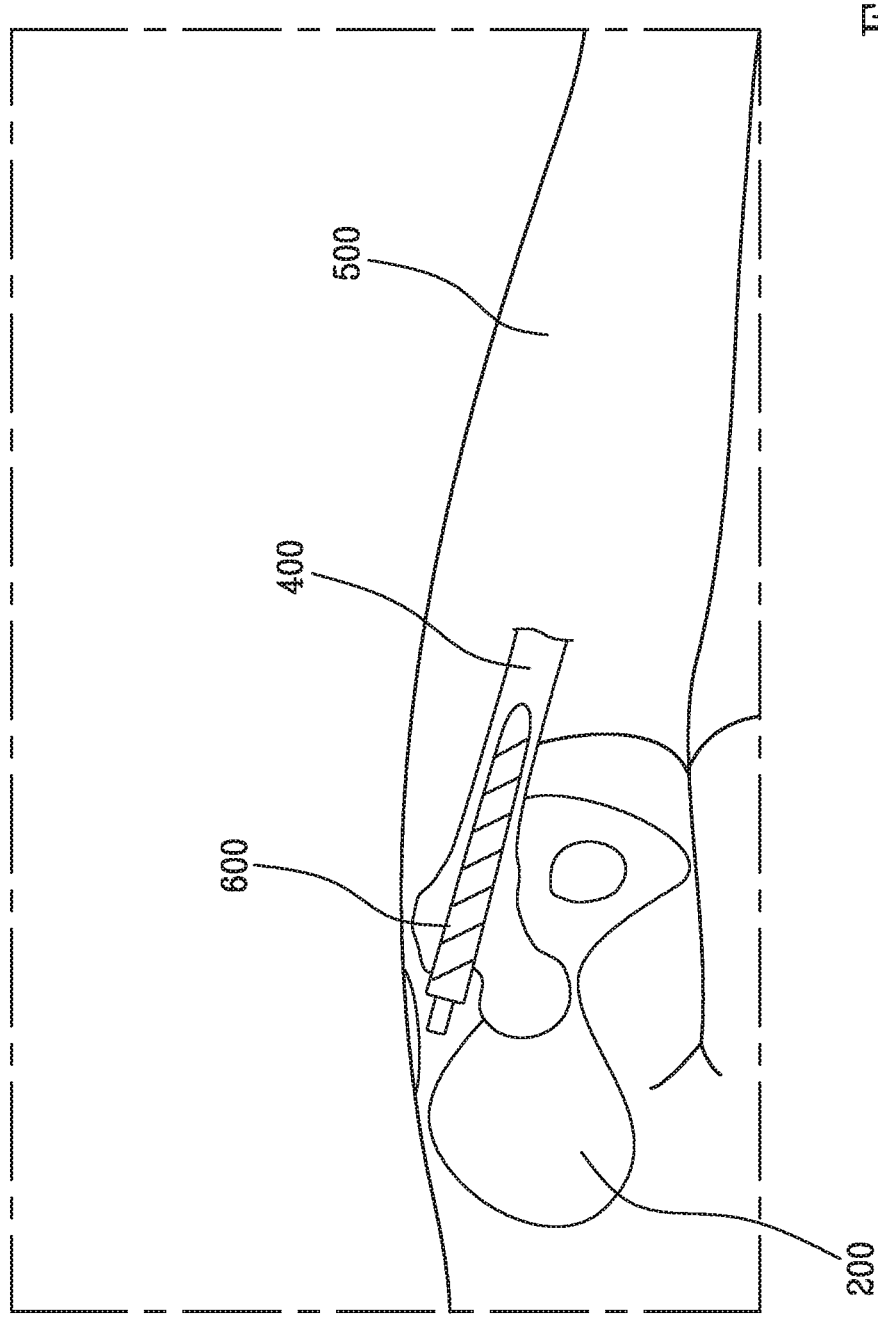
Figure 9:
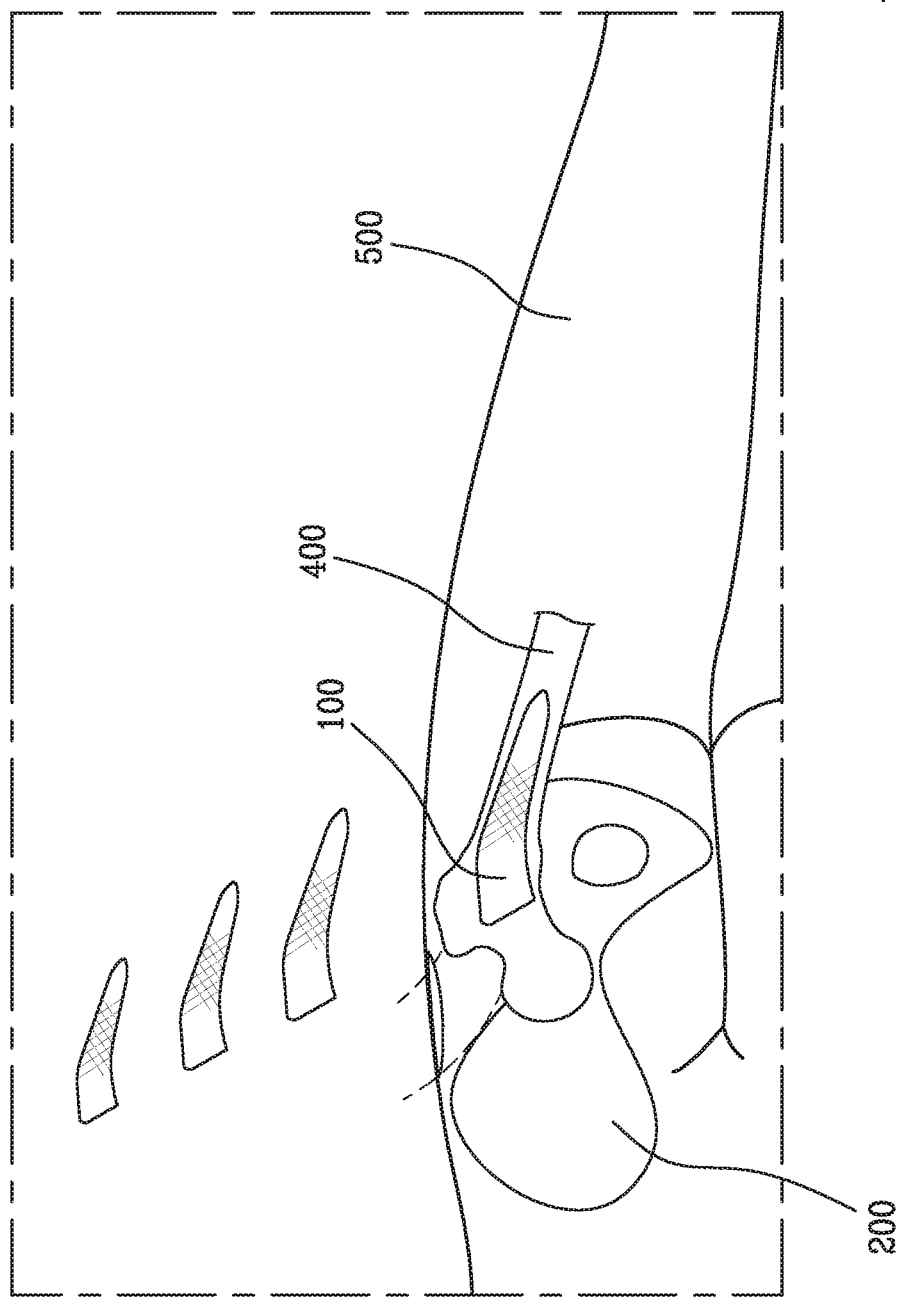

Then the surgeon proceeds with the upper cortical opening of the femur, the proximal reaming of the femur, and the proximal and distal broaching of the femur itself (FIG. 8) for the insertion of a temporary stem 100 (FIG. 9), which will be used during the surgical procedure and then removed for positioning the final stem.

Figure 10:
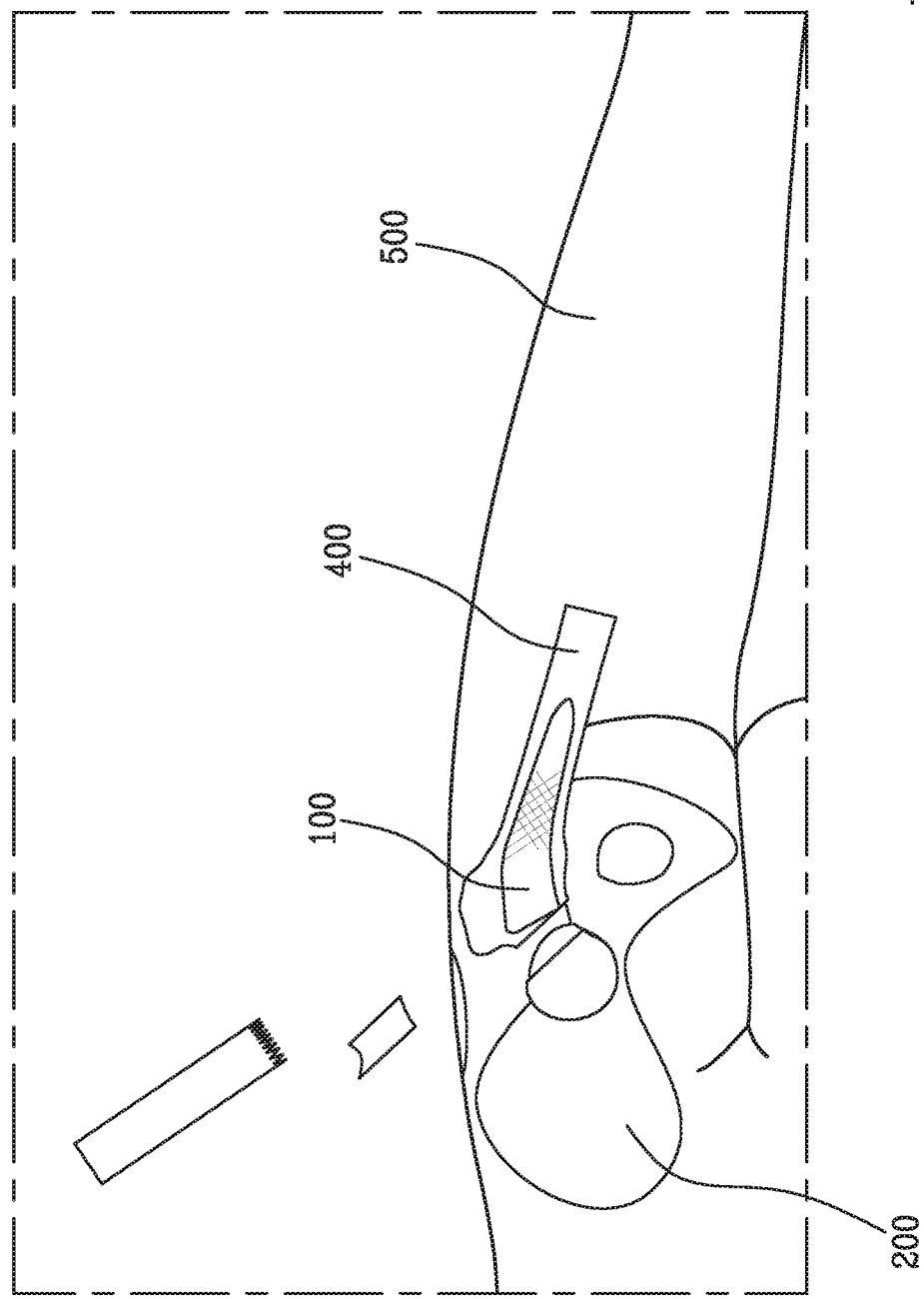
Figure 11:
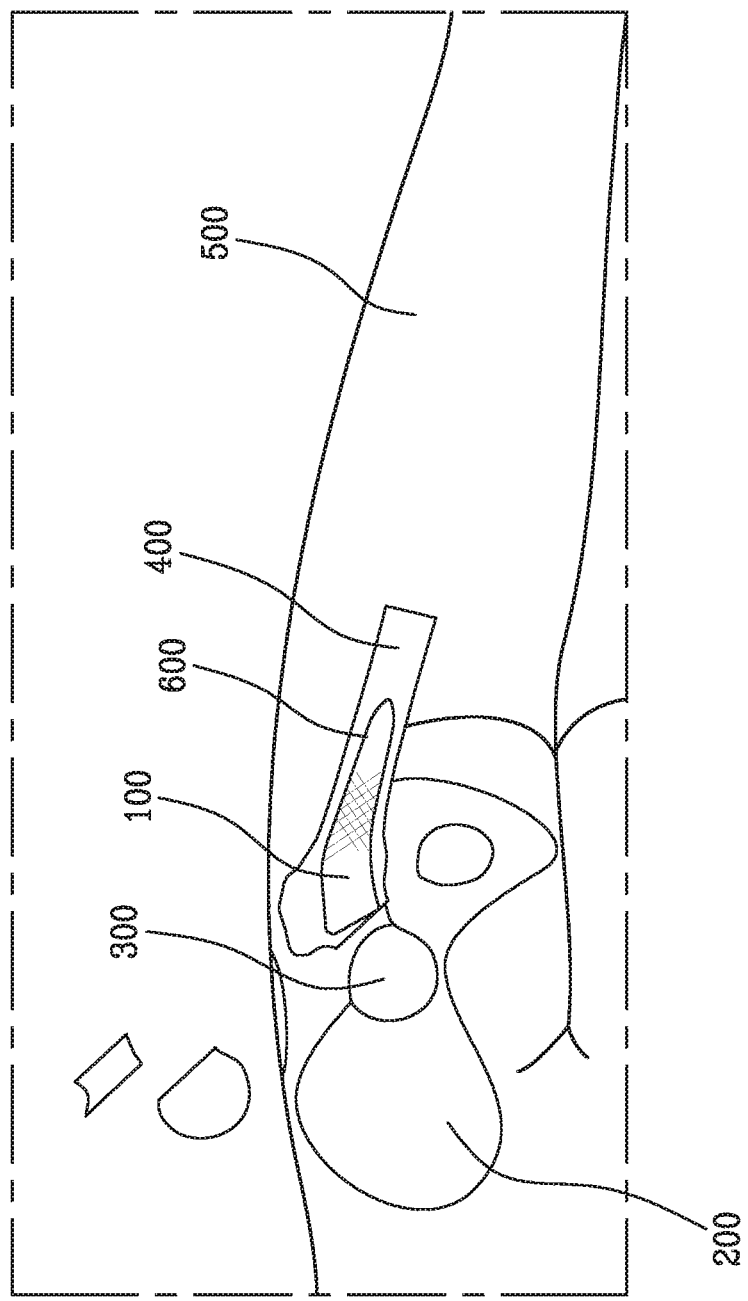
Figure 12:
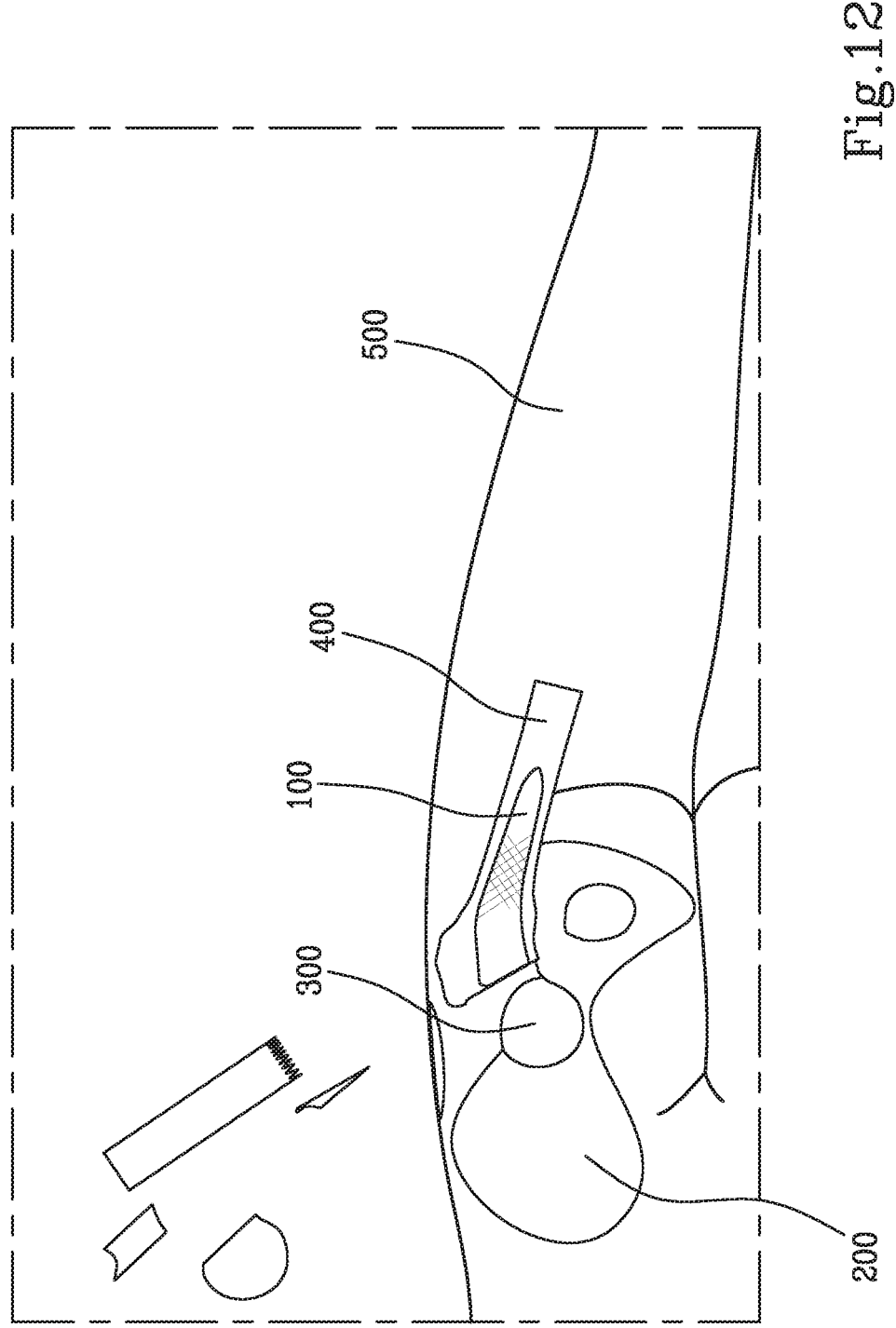
Figure 13:
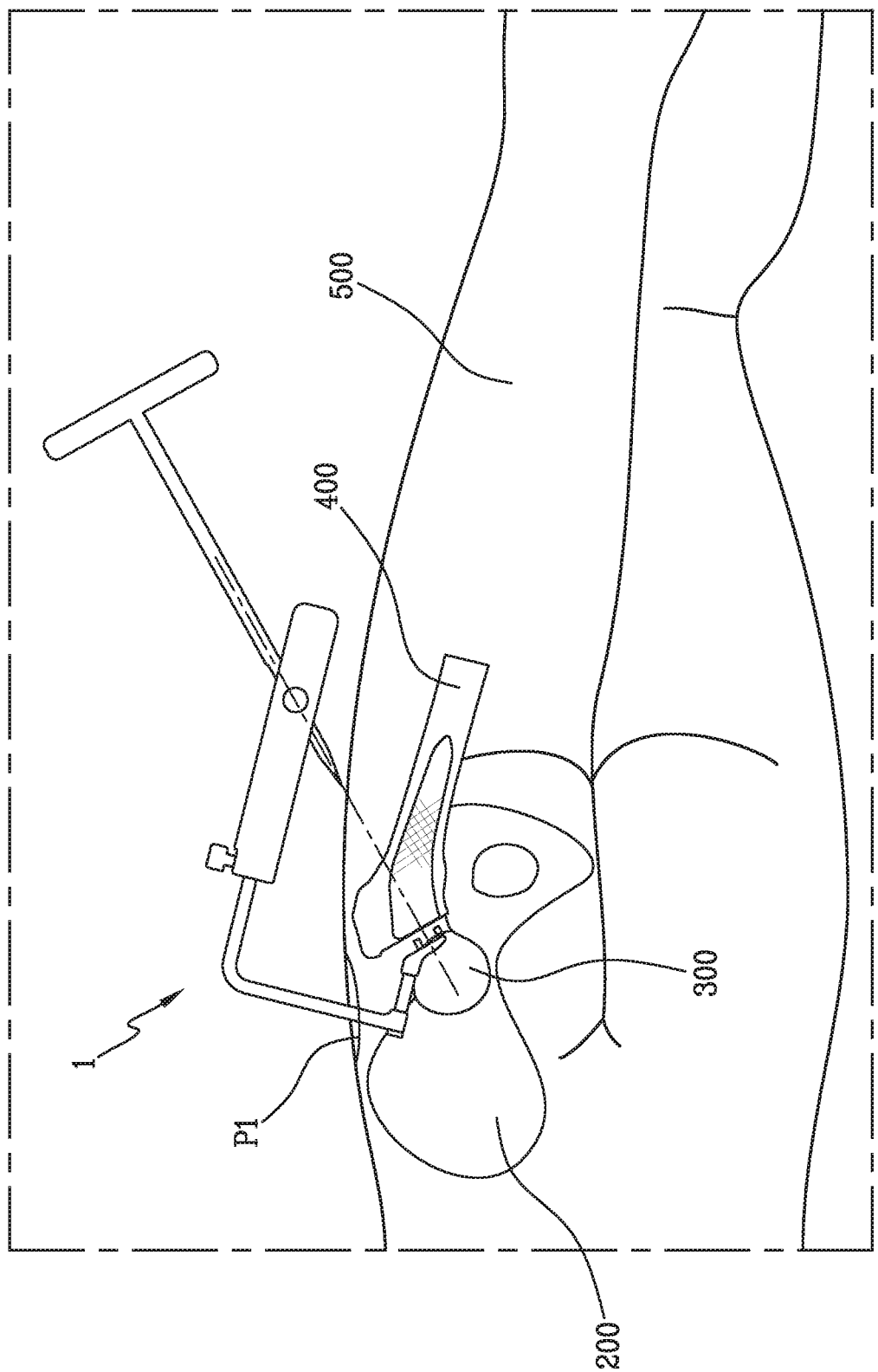

The femoral neck is then cut off (FIG. 10) and the head of the femur is removed from the acetabular cup (FIG. 11). Before inserting the positioning device, which is the subject of this invention, the cut distal part of the femur is trimmed (FIG. 12).

The temporary stem 100 is inserted into the femoral canal at the femur's femoral neck.

The surgeon inserts the first end 3 of the device and, in particular, the positioning and fixing head 12, through the first incision P1 (FIG. 13) to fix the connection means 13 of the head 12 to the temporary stem 100 inserted into the femoral canal (FIG. 14), at the femoral neck.

Figure 14:
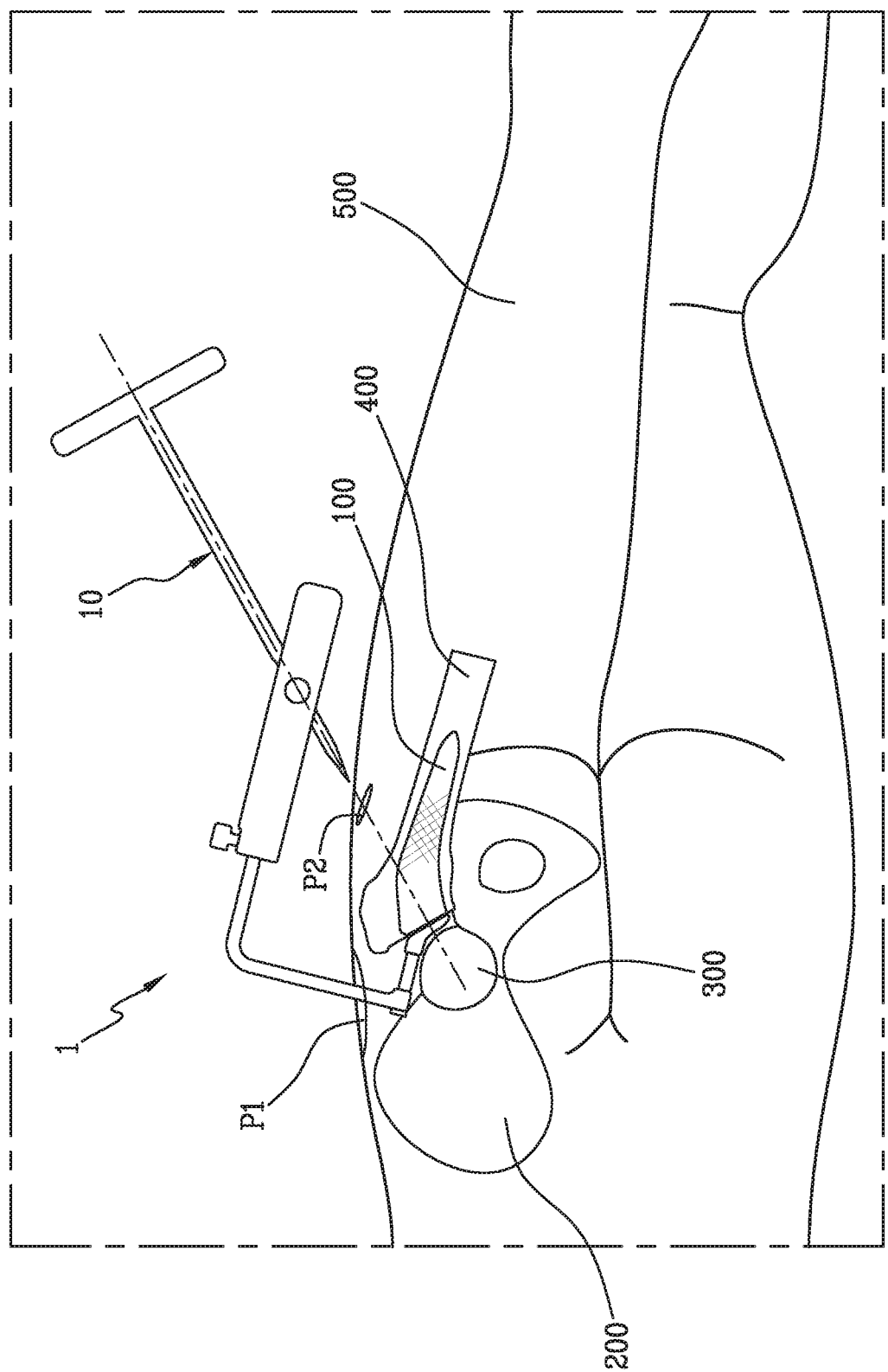
Figure 15:
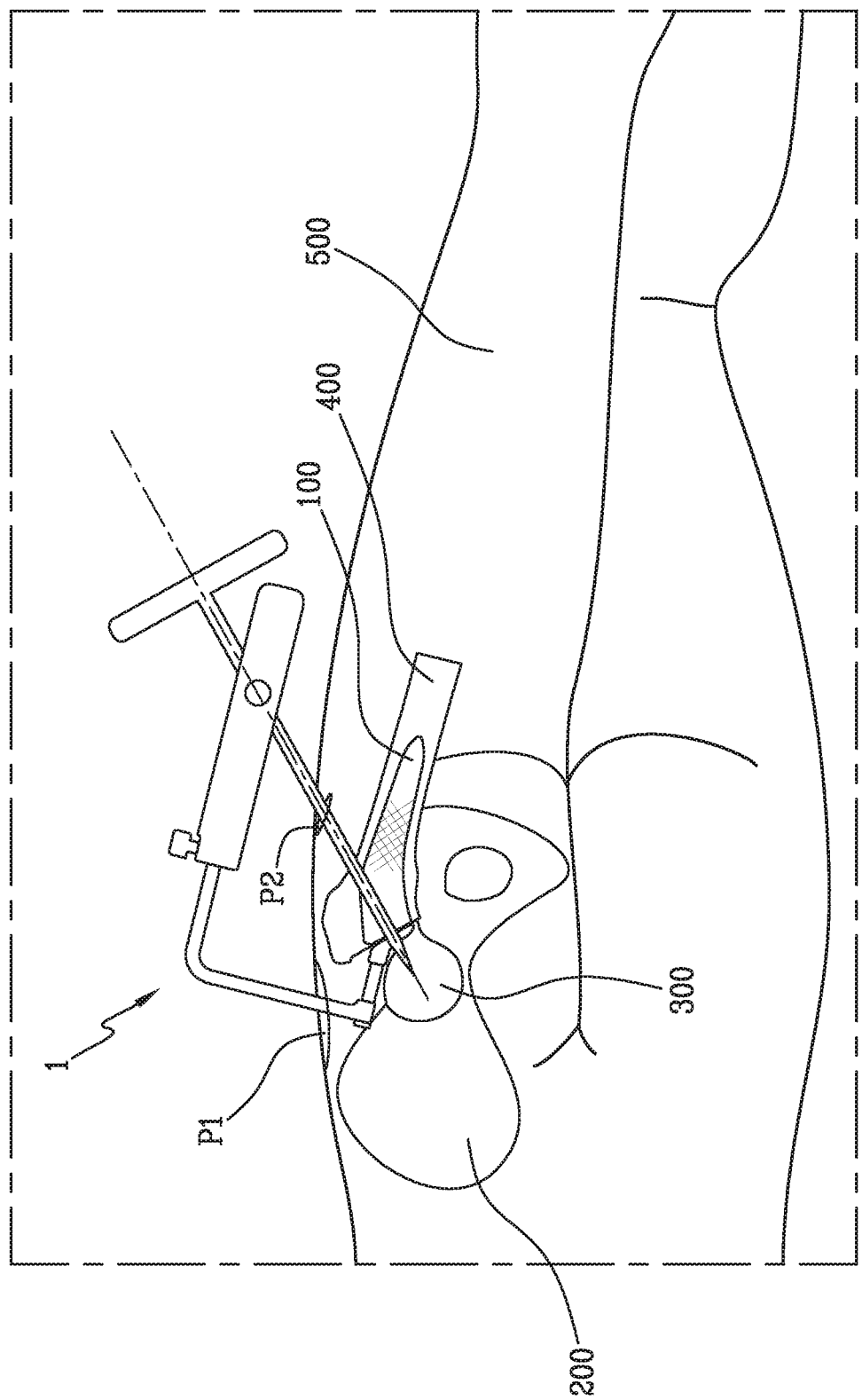

Once the positioning and fixing head 12 has been joined to the temporary femoral stem 100, the arched structure 2 comes out of the patient's body and orients itself by positioning the second end 4 above the patient's leg at the level of the femur (FIG. 14).

The arched structure is positioned on the outside of the leg, on the side opposite the pelvic area.

The position of the gripping element 7 along the third straight segment 23 of the arched structure 2 is adjusted so that the distance of the hinge point of the stem 10, in other words of the seat 9, from the arched portion 6, placed between the second 22 and the third 23 straight segment, is basically equal to the length of the second straight segment 22.

Once the gripping element 7 has been fixed, the stem 10 is tilted to 45° bringing the graduated scale to the zero position and the stem 10 is advanced, again at 45°, towards the patient's leg to make a second incision P2 (FIG. 14). In this way, the stem 10 is aligned with the femoral neck to reach the acetabular cup 300.

Figure 16:
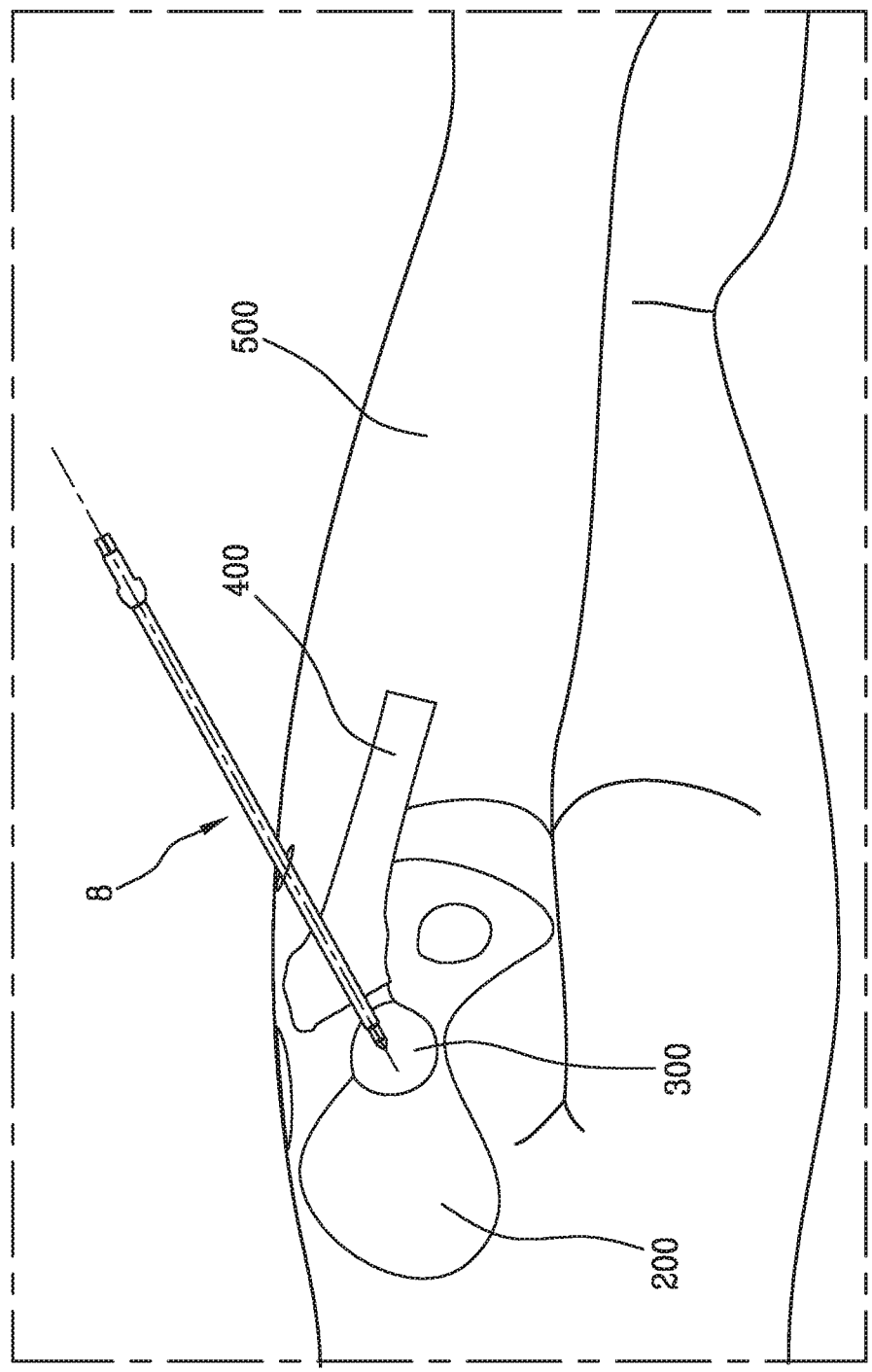
Figure 17:
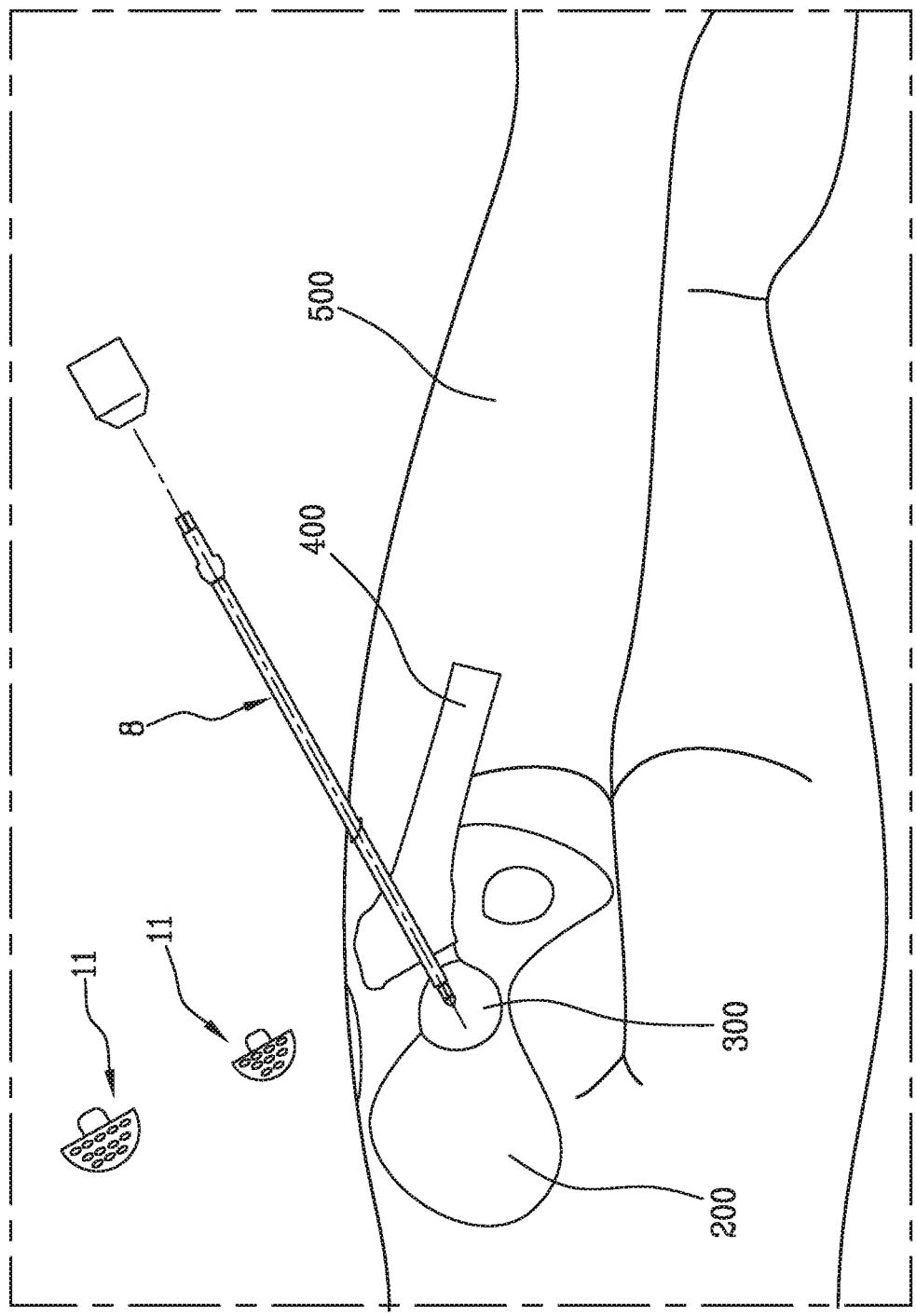

Once the stem 10 is in position (FIG. 15) it is possible to remove the arched structure and proceed by inserting, in succession, the various heads of the surgical tools that will be connected to the stem (FIGS. 16 and 17).

Figure 18:
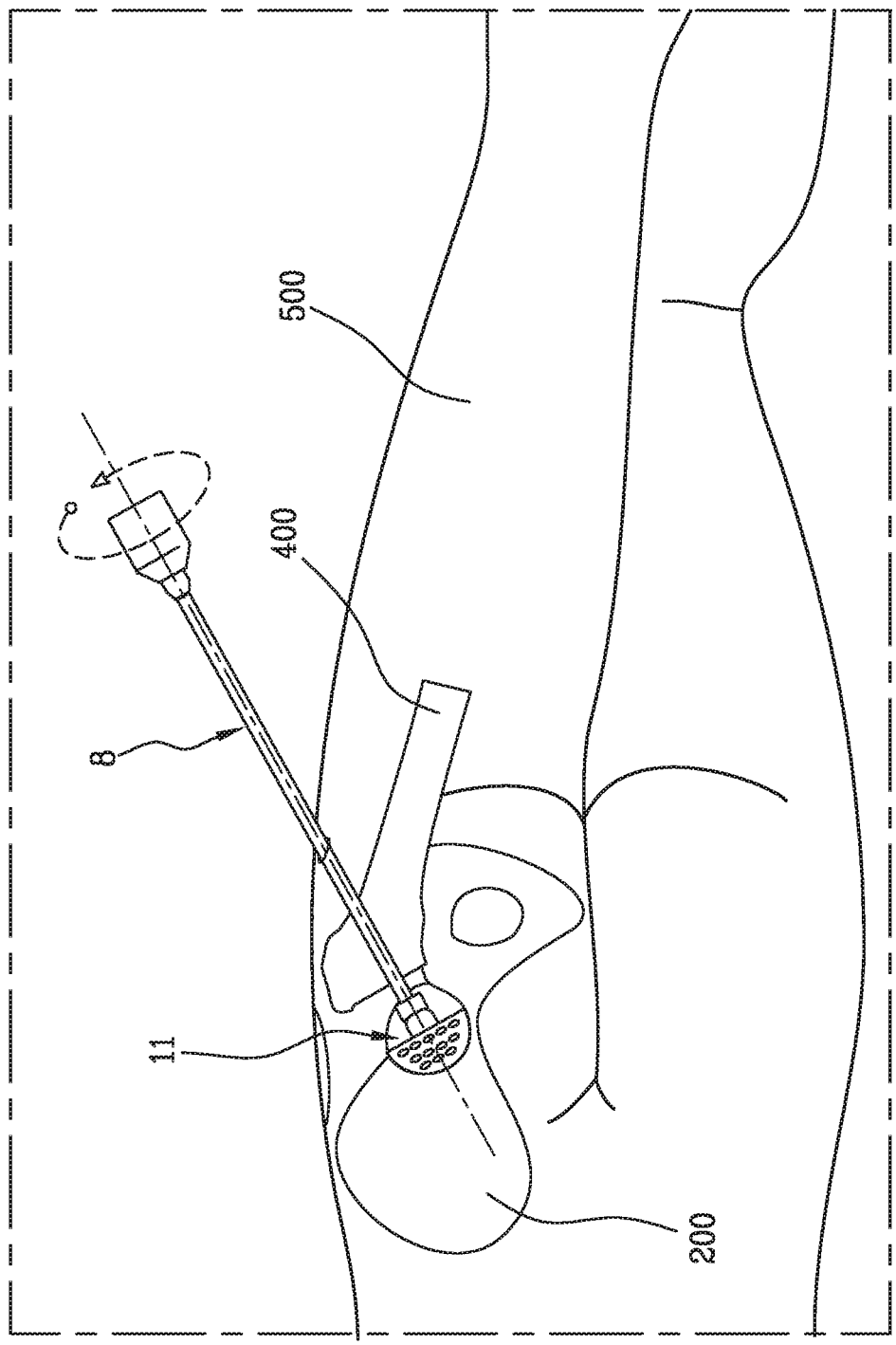

Then the surgeon proceeds with the reaming of the acetabulum to then impact the new acetabular cup (FIG. 18).

The arched structure 2 is advantageously repositioned for the insertion of the fixing screws of the new acetabular cup so that the screwdriver is more stable and more guidable in inserting the screws into the correct position.

Figure 19:
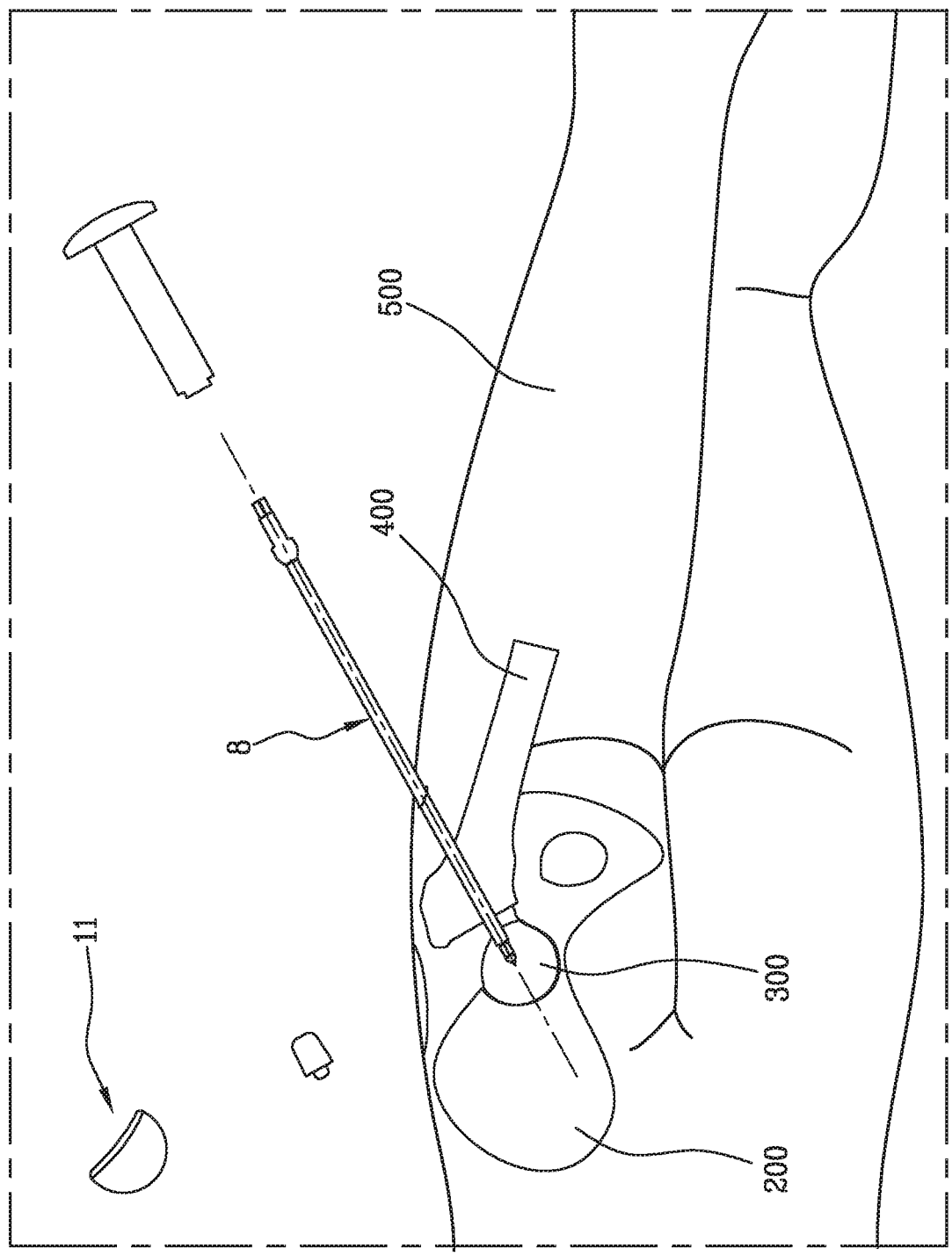
Figure 20:
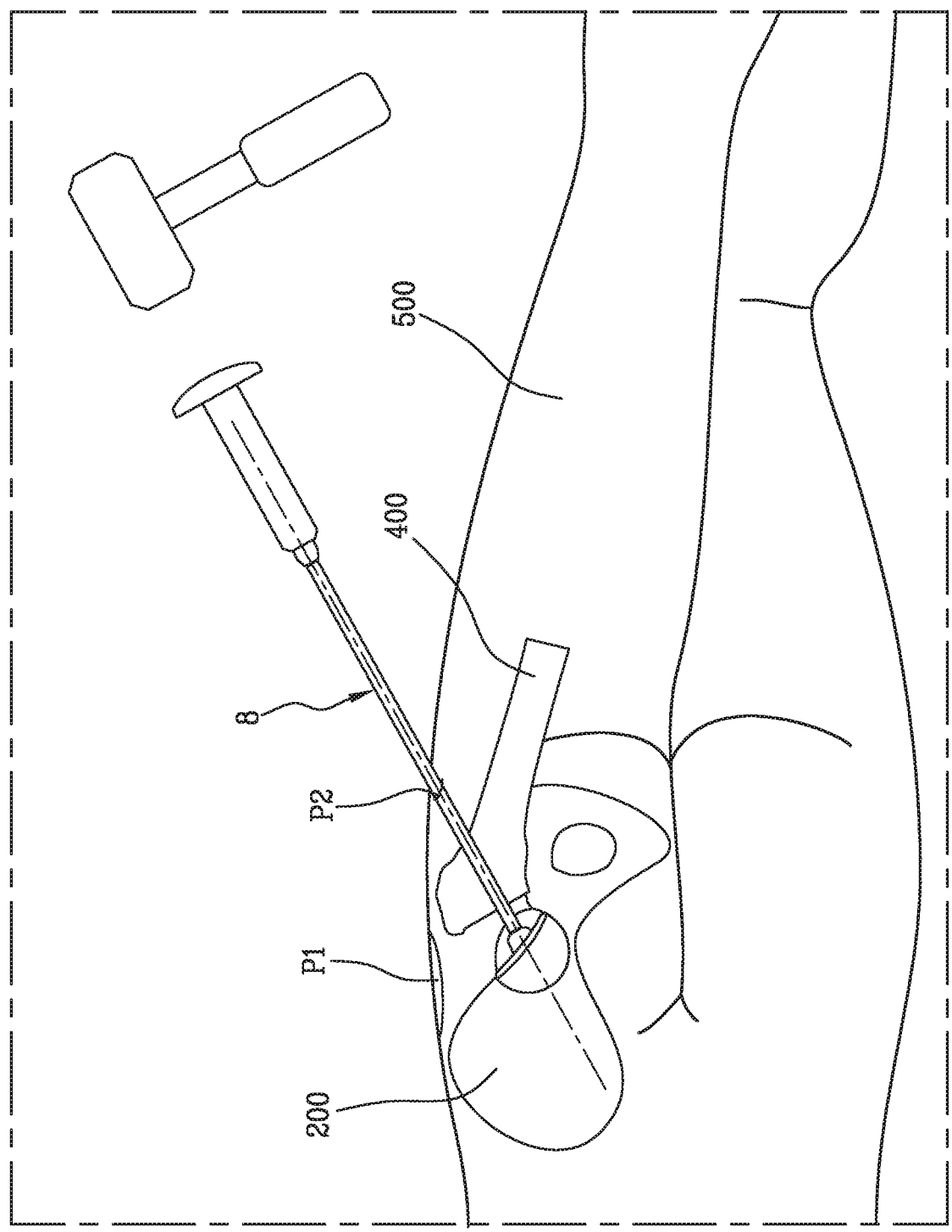

Finally, the entire device and the temporary stem 100, previously fixed in the femur, can be removed to replace it with the definitive stem 700 and, thus, to fix the final implant 800 (FIGS. 19-21).

Compared to what is already known, the positioning device of a surgical instrument for hip arthroplasty surgery, which is the subject of this invention, means that the instrument is more stable and more guidable because the device is fixed directly to the femur.

With the use of this device, the field of vision of the surgical site is not obstructed, as, in contrast, is the case with devices of the prior art, allowing better vision. The direct connection to the femur, instead of to the acetabular cup, leaves the surgeon free to operate directly, and without obstacles, inside the acetabular cup to ream and insert the prosthesis.

The device that is the subject of this invention is easy for the surgeon to use and facilitates quick and safe operations for the patient. The tilting of the stem aligns the instrument with the surgical site and the possibility of moving the stem itself gives the surgeon greater freedom of action.

Finally, the device that is the subject of this invention is able to be configured as a correct and precise reference to the patient's anatomy during hip replacement operations.

The invention claimed is:

1. A positioning device configured to direct and orient a surgical instrument towards an acetabular cup during an operation to reposition and/or replace a hip joint, the positioning device comprising:
    an arched structure having a first end and a second end, said first end configured to be positioned inside a patient;
    a gripping element arranged at said second end of said arched structure, the gripping element being slidably movable along a portion of said arched structure that is aligned with a longitudinal axis of the gripping element and includes the second end, the gripping element defining a slot extending through the gripping element transverse to the longitudinal axis of the gripping element, the slot configured for receiving the surgical instrument; and
    a positioning and fixing head being rotationally coupled at a fixed end thereof to said first end of said arched structure such that a free end of the positioning and fixing head is rotatable about a longitudinal axis of the first end of the arched structure, wherein the free end is spaced apart from and opposite the fixed end along a longitudinal axis of the positioning and fixing head,
    wherein the positioning and fixing head comprises a connection means that faces toward the gripping element, and
    wherein the free end of the positioning and fixing head is movable relative to the arched structure out of a first plane that extends through the arched structure, the gripping element, and the fixed end of the positioning and fixing head.

2. The positioning device according to claim 1, wherein said connection means comprise a snap connection or snap fit.

3. The positioning device according to claim 1, wherein a second plane that axially cuts through the connection means is disposed at an angle of + or −20° relative to the first plane when the free end of the positioning and fixing head is rotated out of the first plane.

4. The positioning device according to claim 1, wherein said arched structure is shaped and sized so as to position said second end above a femur of the patient.

5. The positioning device according to claim 1, wherein said slot is configured to allow a stem of the surgical instrument to be slidably movable within said slot.

6. The positioning device according to claim 5, further comprising the surgical instrument, wherein a stem of the surgical instrument is joined to the gripping element so as to be oriented substantially towards the positioning and fixing head, thus defining an insertion angle ranging between 30° and 60° in relation to the longitudinal axis of said gripping element.

7. The positioning device according to claim 6, wherein the slot is configured to allow the stem of the surgical instrument to have a degree of rotational freedom about an axis that is orthogonal to the stem itself and to the longitudinal axis of said gripping element, said degree of rotational freedom allowing said stem to travel an angle ranging between −15° and +105° in relation to said insertion angle.

8. The positioning device according to claim 6, wherein said insertion angle is 45°.

9. The positioning device according to claim 1, further comprising the surgical instrument, wherein said surgical instrument comprises a plurality of interchangeable heads or tools that can be joined to a stem of the surgical instrument.

10. The positioning device according to claim 1, wherein said gripping element has a circular graduated scale indicating angles of rotational travel of a stem of the surgical instrument.

11. The positioning device according to claim 1, further comprising the surgical instrument having a stem, wherein said gripping element has at least a second degree of rotational freedom about the longitudinal axis thereof, said second degree of rotational freedom allowing said gripping element to travel about said longitudinal axis at an angle of + or −15° in relation to a position at which the stem of the surgical instrument is in the first plane.

12. The positioning device according to claim 1, wherein said arched structure has at least a first, a second, and a third straight segment defining an open arched structure.

13. The positioning device according to claim 12, wherein said first and said second straight segments are orthogonally connected in sequence to each other with a respective arched portion, and said second and said third straight segments are orthogonally connected in sequence to each other with a respective arched portion.

14. The positioning device according to claim 1, wherein said positioning and fixing head lies on a third plane that is tilted in relation to the longitudinal axis passing through the first end of said arched structure by a tilt angle ranging between 5° and 85°.

15. The positioning device according to claim 14, wherein the tilt angle is 45°.

16. A positioning device configured to direct and orient a surgical instrument towards an acetabular cup during an operation to reposition and/or replace a hip joint, the positioning device comprising:
an arched structure having a first end and a second end, said first end configured to be positioned inside a patient;
a gripping element arranged at said second end of said arched structure, the gripping element being slidably movable along a portion of said arched structure that is aligned with a longitudinal axis of the gripping element and includes the second end, the gripping element comprising a seat configured for receiving the surgical instrument; and
a positioning and fixing head being coupled to said first end of said arched structure, wherein the positioning and fixing head comprises connection means that face toward the gripping element,
wherein the seat is configured to receive a stem of the surgical instrument such that the stem is oriented substantially towards the positioning and fixing head and is transverse to the longitudinal axis of the gripping element, and
wherein said gripping element is coupled to the second end of the arched structure such that said gripping element, together with the seat, is separately rotatable about the longitudinal axis of the gripping element without a corresponding rotation of the arched structure.

17. The positioning device according to claim 16, wherein said connection means comprise a snap connection or snap fit.

* * * * *